(12) United States Patent
Stahl et al.

(10) Patent No.: US 7,858,595 B2
(45) Date of Patent: Dec. 28, 2010

(54) ANTI-INFECTIOUS CARBOHYDRATES

(75) Inventors: Bernd Stahl, Rosbach (DE); Berndt Finke, Herford (DE); Joachim Schmitt, Hösbach (DE); Werner Goebel, Gerbrunn (DE); Jörg Slaghuis, Würzburg (DE)

(73) Assignee: N.V. Nutricia (NL)

( * ) Notice: Subject to any disclaimer, the term of this patent is extended or adjusted under 35 U.S.C. 154(b) by 757 days.

(21) Appl. No.: 10/490,102

(22) PCT Filed: Sep. 25, 2002

(86) PCT No.: PCT/EP02/10761

§ 371 (c)(1),
(2), (4) Date: Aug. 11, 2004

(87) PCT Pub. No.: WO03/028738

PCT Pub. Date: Apr. 10, 2003

(65) Prior Publication Data

US 2005/0004070 A1    Jan. 6, 2005

(30) Foreign Application Priority Data

Sep. 25, 2001  (DE)  ................. 101 47 100

(51) Int. Cl.
*A61K 31/715*  (2006.01)
*A61K 31/70*   (2006.01)
*C07H 5/06*    (2006.01)
*C07H 1/00*    (2006.01)
*A23G 3/00*    (2006.01)

(52) U.S. Cl. .................. 514/54; 514/62; 536/55.2; 536/123.1; 426/658

(58) Field of Classification Search ................ 536/55.2, 536/123.1; 514/54, 62; 426/658
See application file for complete search history.

(56) References Cited

U.S. PATENT DOCUMENTS

| | | | | |
|---|---|---|---|---|
| 4,971,956 A | * | 11/1990 | Suzuki et al. | 514/55 |
| 5,294,537 A | * | 3/1994 | Batt | 435/7.32 |
| 6,045,854 A | * | 4/2000 | Prieto et al. | 426/658 |
| 6,146,670 A | * | 11/2000 | Prieto et al. | 426/72 |

OTHER PUBLICATIONS

Gibson et al, "Regulatory Effects of Bifidobacteria on the Growth of Other Colonic Bacteria", Journal of Applied Bacteriology, 1994, vol. 77, pp. 412-420.*

* cited by examiner

*Primary Examiner*—Shaojia Anna Jiang
*Assistant Examiner*—Everett White
(74) *Attorney, Agent, or Firm*—Bacon & Thomas, PLLC

(57) ABSTRACT

Neutral straight-chain or branched oligosaccharides for preventing the invasion and infection of mammal cells by pathogens and for fighting diseases caused by such pathogens are disclosed. Food, dietetic products and pharmaceutical agents containing oligosaccharides consist of a base unit of formula (I), and between 0 and 19 other units of formula (II), which are linked directly or indirectly to the base unit. Gal represents a galactose monosaccharide unit; Glc represents a glucose monosaccharide unit; HexNAc rpresents an N-acetylated galactosamine or glucosamine monosaccharide unit (GalNAc or GlcNAc); R independently represent a β 1-3 or β 1-6 glycosidic link to HexNAc monosaccharide of the next [Gal-HexNAc] unit (II), and on a terminal [Gal-HexNAc] unit, or R are not present; and a terminal [Gal-HexNAc] unit, wherein R represent a deoxyhexose radical, can have another deoxyhexose radical on the HexNAc monosaccharide unit.

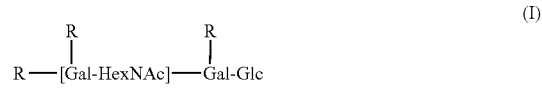

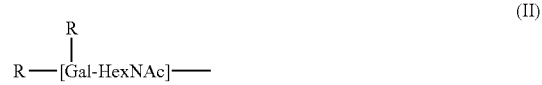

6 Claims, No Drawings

ANTI-INFECTIOUS CARBOHYDRATES

DESCRIPTION

The invention relates to the use of neutral straight-chain or branched oligosaccharides for preventing the invasion and infection of mammal cells by pathogens, and for combating diseases caused by such pathogens. The invention also relates to food, dietetic and pharmaceutical agents containing these oligosaccharides.

The adhesion of pathogenic organisms, as well as of cell-damaging substances to the surface of mammal cells is the first step and an essential prerequisite for an infection or impairment of the cell. The interaction between the pathogens and the cells comes about through a ligand-receptor relationship. Glycostructures play an important role in these relationships or interactions.

One possibility to influence such ligand-receptor relationships consists in blocking and/or structurally changing the respective receptors on the cell surface or of the ligands.

In specific test systems, various carbohydrate mixtures have proven to be very effective in reducing or completely preventing the adhesion, for example of micro-organisms to the cell surface, cf. Kunz, C.; Rudloff, S. *Acta Paediatr.* 1993, 82, 903-912. Other substances such as the Lewis structures as carbohydrate ligands of selectines (adhesion proteins on endothelia and lymphocytes) modulate the interaction between the lymphocytes and the endothelium, for example, in the context of rolling, homing and the invasion with inflammatory processes (Norman, K. E.; Anderson, G. P.; Kolb, H. C.; Ley, K.; Ernst, B. *Blood* 1998, 91, 475-483). A further important physiological role in connection with basic cellular functions, as well as with specific functions such as cell adhesion, migration, chemotaxis, proliferation, apoptose, neurite growth, are fulfilled by galactose-recognizing lectines, called galectines (Cooper D N & Barondes S H, *Glycobiology*, 1999 9 (10) 979-984). It could be shown for the nematode *C. elegans* that its galectine LEC-1 can bind various galactose-containing oligosaccharide derivatives with different specificity (Arata Y. Hirabayashi J. Kasai K, *JBC*, 2001:276, 5, 3068-3077). In a model test with mice, the lethality of an experimental listeriose could be reduced using galactose-specific lectines (Stoffel, B., Beuth J., Pulverer G., *Zentralbl. Bakteriol.*, 1996, 284:439-442). The adherence of micro-organisms to host cells, however, may also be the trigger of signal cascades both in the exogenous pathogens and in the endogenous cells.

Another possibility consists in achieving an influence on molecular processes on the molecular biological level. This may lead to, for instance in the case of mammal cells, defence mechanisms being triggered, or, in the case of pathogenic micro-organisms, the expression of virulence mechanisms (e.g. cutting off virulence genes in bacteria by blocking central regulators) being reduced or prevented. In this way, the expression of certain surface structures of pathogenic *listeria* bacteria that are responsible for the invasion in host cells, may be successfully inhibited by certain carbohydrates such as cellobiose (Park S F, Kroll R H, *Mol Microbiol*, 1993 8:653: 661; WO-A 94/02586).

It is the object of the present invention to demonstrate a way how, with the aid of oligosaccharides, the invasion and infection of mammal cells by pathogens may be reduced or prevented, and how diseases caused by such pathogens may be effectively combated.

This object is fulfilled by the teaching of the claims.

According to the invention, specific oligosaccharides are used to achieve the object of the invention. These oligosaccharides are referred to below as inventive oligosaccharides.

According to the invention, single inventive oligosaccharides may be used alone, or several inventive oligosaccharides combined. Moreover, it is possible to use an inventive oligosaccharide or several inventive oligosaccharides, or indeed a combination of a number of inventive oligosaccharides together with other carbohydrates not figuring among the inventive oligosaccharides, in the form of a carbohydrate mixture.

The inventive oligosaccharides have a base unit of the following general formula I:

wherein Gal represents a galactose monosaccharide unit, Glc represents a glucose monosaccharide unit, and HexNAc represents an N-acylated galactosamine monosaccharide unit or glucosamine monosaccharide unit (which may also be abbreviated as GalNAc or GlcNAc).

The residues R in general formula I do not have to be present, with the hydrogen atom not being considered as a residue within the framework of the present documents. Simply structured inventive oligosaccharides are thus those having the following general formula

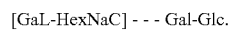

Lacto-N-tetraose (Gal β1-3GlcNAcβ 1-3Galβ1-4Glc, LNT) which is preferred according to the invention, counts among these oligosaccharides.

In these latter oligosaccharides, the [Gal-HexNAc] unit represents a terminal unit. Same can be linked to the galactose monosaccharide unit (Gal) with one deoxyhexose (preferably an α1-2 glycosidic bond) or with two deoxyhexoses. The residue R or the residues R in the general formula I may thus represent in this case such a deoxyhexose residue that is preferably a rhamnose and fucose residue.

The lacto-N-tetraose that is preferred according to the invention, counts among these latter compounds, which lacto-N-tetraose is derivatized in an α1-2 glycosidic linkage at the terminal galactose monosaccharide unit of the [Gal-HexNAc] unit by means of fucose, in this case lacto-N-fucopentaose I (LNFP I).

The residues R of the basic unit of the general formula I may also represent linkage points to further [Gal-HexNAc] units of the following general formula II:

The residues R of these [Gal-HexNAc] units of the general formula II that are directly bound to the base unit of the general formula I (one or two residues R may be present per unit) may in turn represent linkage points to further [Gal-HexNAc] units of the general formula II, which further units are then indirectly bound to the base unit of the general formula I. Also the further [Gal-HexNAc] units of the general formula II may again feature such linkage points, and so on, the [Gal-HexNAc] units being bound through a β 1-3 or β 1-6 glycosidic linkage. Among those oligosaccharides count, for example, those of the following general formulae, to name just a few:

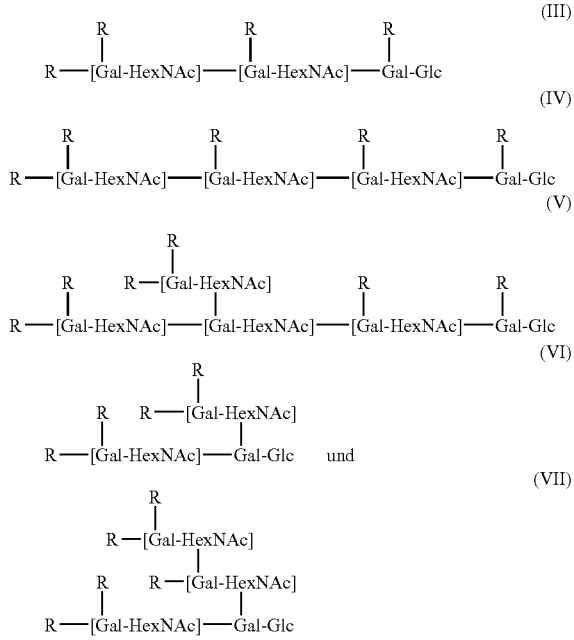

The residues R in these formulae have the meanings indicated above. Thus, for example, all of the residues R may not be present. Furthermore, one or both of the residues R, or all of the residues R may represent a linkage to the next [Gal-HexNAc] unit, which in turn each may have one residue R or two residues R, or else do not have any such residue R. All in all, up to 20 [Gal-HexNAc] units, and hence 1, 2, 3, 4, 5, 6, 7, 8, 9, 10, 11, 12, 13, 14, 15, 16, 17, 18, 19 and 20 of such units may be present in the inventive oligosaccharides, with the first such unit belonging to the base unit of the general formula I, and the up to 19 further units of this type corresponding to the general formula II. The inventive oligosaccharides thus may represent straight-chain or branched molecules.

Assuming for explanation purposes that in the above formulae (III) to (VII), none of the residues R represents a linkage to the next [Gal-HexNAc] unit, then the compounds of formulae (III) and (IV) each have only one terminal [Gal-HexNAc] unit, i.e. that shown furthest to the left, whereas the other units are in the middle position. The compounds of formulae (V), (VI) and (VII) each have two terminal units of this type, with compound (V) also having two, and compound (VII) having one unit of the general formula II located in the middle. In these terminal units, the residues R may also represent a deoxyhexose residue. Thus, one, two, three (if present) or all of the terminal [Gal-HexNAc] units of the inventive oligosaccharides may have one deoxyhexose residue of this type or two residues of this type.

In addition, one or more (if present) terminal [Gal-HexNAc] unit(s), in which the residue(s) R represent(s) a deoxyhexose residue, may have a further deoxyhexose residue at the HexNAc monosaccharide unit.

The inventive oligosaccharides preferably include those oligosaccharides which meet one, two, three or even all four of the following criteria:

the deoxyhexose residue, if present, of the galactose monosaccharide unit of the terminal [Gal-HexNAc] unit(s) is linked to it in an α1-2 glycosidic bond,
the deoxyhexose residue, if present, of the galactose monosaccharide unit of the terminal [Gal-HexNAc] unit(s) is a rhamnose and fucose residue,
the further deoxyhexose residue, if present, of the HexNAc monosaccharide unit of the terminal [Gal-HexNAc] unit(s) is linked to it in an α1-3 or α1-4 glycosidic bond,
the further deoxyhexose residue, if present, of the HexNAc monosaccharide unit of the terminal [Gal-HexNAc] unit(s) is a rhamnose and fucose residue.

The inventive oligosaccharides are, incidentally, known compounds. Thus, the oligosaccharides LNT and LNFP I used according to the invention, count among the oligosaccharides that are present in human milk.

Surprisingly, it has been found that the inventive oligosaccharides at least reduce or even prevent the invasion and infection of mammal cells, and may be used for combating diseases caused by such pathogens. These pathogens include invasive Gram-positive and Gram-negative pathogenic bacteria, e.g. intracellular bacteria, in particular *listeria* bacteria and pathogenic viruses, e.g. rotaviruses.

It has been found, for example, that the inventive oligosaccharides may prevent the invasion and infection of mammal cells by *listeria* bacteria, in particular *Listeria monocytogenes*. The results of the studies conducted clearly show that neither the process of phagocytosis as such, nor the replication of the ingested *listeria* bacteria taken is inhibited. The inventive oligosaccharide LNFP I, among others, turned out to have a particularly strong inhibitory effect.

The pentasaccharide LNFP I thus showed a strong, yet dose-dependant inhibitory action against *listeria* bacteria. Constitutional isomer compounds to LNFP I, to which, for example, the oligosaccharides LNFP II and LNFP III and LNFP V belong, in contrast did not shown any such action. Incidentally, the oligosaccharides LNFP II and LNFP III are, like LNFP I, also present in human milk.

The inventive oligosaccharides may not only be used as free oligosaccharides (i.e. having a reducing end) but may also be used immobilized on or adsorbed in a carrier. This carrier may be a peptide/protein (e.g. BSA), a lipid (glycolipid, ceramide), a polymer or a bio-polymer (e.g. carbohydrate dendrimer, polysaccharide, polyacrylamide) or any other aglykone.

The inventive oligosaccharides, be they free oligosaccharides or oligosaccharides bound on a carrier, may be incorporated into various foods, dietetic and pharmaceutical compositions. All of these compositions may be present in liquid or solid form. The term food used herein includes not only the foodstuff itself, but also nutritional supplements, drinks, as well as foods including infant and baby formulae. The term baby formulae or infant formulae comprises all artificially produced foods, but not human milk. "Artificial" here means those foods that are produced from raw materials of vegetable and animal origin, but not of human origin. These foods may be administered to a human or an animal in any desired manner. This also includes the administration as tube feeding into the stomach.

The inventive oligosaccharides may, for example, be added as admixtures or additives to the following products, although this enumeration is not conclusive: milk and milk products, infant and baby formulae, chocolate bars, yoghurt drinks, cheese, sausage and meat products, anabolic food, probe food and products for pregnant women.

The inventive oligosaccharides may also be administered in the form of a pharmaceutical composition alone or together with one or several additional active agent(s). They may, for example, be formulated as a tablet/sachet. For the formulation of such pharmaceuticals, usual adjuvants, carriers, auxiliary agents, diluents, moisturizing agents, thickening agents, flavoring agents, sweetening agents, etc. may be used.

The pharmaceutical compositions may be administered in any usual way to a patient (i.e. human or animal). However, for the sake of convenience these are compositions suited for the oral, lingual, nasal, intestinal, bronchial, vaginal, topical (skin and mucosa) and per os administration, and are formulated according to the kind of administration.

The food, dietetic and pharmaceutical compositions containing at least one inventive oligosaccharide may be used among other things for the prevention and treatment of infections of the gastrointestinal tract, e.g. in case of listerioses, of the blood system, the respiratory passages, the urogenital tract, as well as the nasopharynx, and for protecting endothelia, epithelia and mucosa. They may thus also be applied topically to the skin or may also be used on mucous membranes. These mucous membranes include the nasal, intestinal, bronchial and vaginal mucous membranes. The inventive oligosaccharides may for instance be added to a mouth wash. All age groups, ranging from new born babies up to senior citizens, may be mentioned as/are potential target groups for the inventive oligosaccharides. Particular fields of application are the protection and treatment of pregnant women, the sick as well as debilitated and elderly people, for whom the prevention e.g. of a listeriosis is of a particular importance.

The inventive oligosaccharides and, for example LNFP I are prepared chemically, enzymatically or using a combination of these two technologies according to suitable known methods. This takes place in a systematic manner from monosaccharide components or by modifying suitable oligosaccharide raw materials. In the enzymatic syntheses, both transferases (Leloir or non-Leloir) and hydrolases (reverse hydrolysis or transglycosilation) are used. The enzymes, may in this case be both free as well as bound (for instance, membrane reactor), or may be covalently bound to a carrier (e.g. beads, chromatography material or filtration membranes). It is also possible to use procaryont or eucaryont cells for the synthesis, provided these cells have the suitable enzymes. For further details for preparing the inventive oligosaccharides, reference is made for example to *Carbohydrates in Chemistry and Biology* (editors Ernst, Hart, Sinay, Wiley VCH-Weinheim 2000, Vol. I-IV).

Exemplary dietetics and pharmaceuticals containing the inventive oligosaccharides are given below.

EXAMPLE 1

For preparing sachets, in each case 100 mg LNFP I are mixed in a dry state with 990 mg of maltodextrine, and then are packed in sachets. These sachets are administered three times per day during meals.

EXAMPLE 2

A known medicinal food (i.e. Milupa® HN 25, balanced diet) in the form of a bead product containing 18.8 g of protein, 8.6 g of fat, 62.8 g of carbohydrates, 3.3 g of minerals and vitamins, is admixed in a preparation known per se with LNFP I in such an amount that 50 mg of LNFP I are contained in 100 g of the finished bead product.

For the preparation of a liquid medicinal food, 100 ml of the known medicinal food Milupa HN 25 liquid (2.3 g of protein, 1.6 g of fat, 8.5 g of carbohydrates, 37 g of minerals and vitamins) are admixed with 7 mg of LNFP I.

EXAMPLE 3

A product for pregnant women

An effervescent tablet (final weight 4.15 g) (Neovin® from Milupa) is prepared in a manner known per se by admixing 200 to 500 mg of LNFP I. One tablet per day is dissolved in 150 ml water and swallowed.

EXAMPLE 4

A product for the elderly and debilitated persons

A balanced pulverized medicinal food (Dilsana® from Milupa) containing 22.5 g of protein, 7.7 g of fat, 60.8 g of carbohydrates, 5.4 g of minerals and vitamins is prepared in a manner known per se by incorporating 100 mg to 1000 mg LNFP I per 100 g of powder. Up to 3×50 g per day of the food are dissolved in 150 ml water and administered.

EXAMPLE 5

Tea 100 g of an instant tea powder prepared in a usual manner are mixed with 2 g of LNFP I. 3.8 g of tea powder are dissolved in 100 ml of hot water, and administered three times per day.

EXAMPLE 6

A protein-adapted infant milk formula (Aptamil® from Milupa) containing 11.8 g of protein, 56.9 g of carbohydrates, 24.9 g of fat, 2.5 g of minerals and vitamins and 45 mg of taurine are prepared in the usual manner in the form of a bead product, which is mixed with 100 mg to 1000 mg of LNFP I per 100 g of infant milk formula.

The invention claimed is:

1. A method for treating an infection caused by *Listeria* bacteria in a patient, comprising:
   administering to said patient in need thereof a composition comprising an effective amount of isolated neutral straight-chain or branched oligosaccharides of a base unit of formula I:

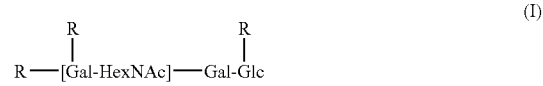

(I)

and 0 to 19 further units linked thereto having a formula of formula II:

(II)

wherein
   Gal represents a galactose monosaccharide unit,
   Glc represents a glucose monosaccharide unit,
   HexNAc represents an N-acetylated galactosamine monosaccharide or glucosamine monosaccharide unit (GalNAc or GlcNAc),
   R is present or not present, and independently a β1-3 or β1-6 glycosidic bond to the HexNAc monosaccharide unit of the next [Gal-HexNAc] unit of formula II, and at a terminal [Gal-HexNAc] unit, a first deoxyhexose residue linked to the galactose monosaccharide unit of said terminal [Gal-HexNAc] unit, and a terminal [Gal-HexNAc] unit, wherein R is a first deoxyhexose residue, and wherein the HexNAc monosaccharide unit optionally has a second deoxyhexose residue, and wherein the patient is pregnant, debilitated, sick, elderly, or an infant.

2. The method according to claim 1, wherein the infection is Listeriosis.

3. The method according to claim 1, wherein the oligosaccharides are administered in an amount of at least 1 mg per kg of body weight and per day to a human or an animal.

4. The method according to claim 1, wherein the *Listeria* bacteria is *Listeria monocytogenes*.

5. The method according to claim 1, wherein the oligosaccharides are isolated lacto-N-fucopentaose or isolated lacto-N-tetraose.

6. The method according to claim 1, wherein the oligosaccharides are isolated lacto-N-fucopentaose I and said isolated lacto-N-fucopentaose I is immobilized on or absorbed on a carrier.

* * * * *